(12) United States Patent
Hasty et al.

(10) Patent No.: US 12,239,496 B2
(45) Date of Patent: Mar. 4, 2025

(54) STETHOSCOPE CLEANING DEVICE (71) Applicant: ORLANDO HEALTH, INC., Orlando, FL (US)

(72) Inventors: Christopher Hasty, Orlando, FL (US); Matthew Solar, Orlando, FL (US)

(73) Assignee: Orlando Health, Inc., Orlando, FL (US)

( * ) Notice: Subject to any disclaimer, the term of this patent is extended or adjusted under 35 U.S.C. 154(b) by 33 days.

(21) Appl. No.: 18/328,087

(22) Filed: Jun. 2, 2023

(65) Prior Publication Data
US 2023/0390023 A1  Dec. 7, 2023

Related U.S. Application Data

(60) Provisional application No. 63/348,175, filed on Jun. 2, 2022.

(51) Int. Cl.
*A61B 90/70* (2016.01)
*A61B 7/02* (2006.01)
*B08B 3/02* (2006.01)

(52) U.S. Cl.
CPC .............. *A61B 90/70* (2016.02); *A61B 7/02* (2013.01); *B08B 3/02* (2013.01)

(58) Field of Classification Search
None
See application file for complete search history.

(56) References Cited

U.S. PATENT DOCUMENTS

| | | | |
|---|---|---|---|
| 2010/0116300 A1* | 5/2010 | Perlman | A61B 90/70 134/133 |
| 2012/0051969 A1* | 3/2012 | Nahman | A61B 7/02 422/28 |
| 2018/0008738 A1* | 1/2018 | Kolins | A61B 7/02 |

* cited by examiner

*Primary Examiner* — Eric W Golightly
(74) *Attorney, Agent, or Firm* — Crowell & Moring LLP

(57) ABSTRACT

A stethoscope cleaning device may include one or more of the following features: a first portion configured for supporting a stethoscope, wherein the first portion includes an earpiece chamber for receiving an earpiece of the stethoscope; and a second portion configured for receiving a container. The first portion may be movable (e.g., pivotable) relative to the second portion, and movement of the first portion relative to the second portion may cause a cleaning fluid to flow from the container to the earpiece chamber.

17 Claims, 7 Drawing Sheets

STETHOSCOPE CLEANING DEVICE

CROSS-REFERENCE TO RELATED APPLICATIONS

This application claims the benefit of and priority to U.S. Provisional Application No. 63/348,175, filed on Jun. 2, 2022, the entirety of which is incorporated herein by reference.

TECHNICAL FIELD

The present disclosure relates to a cleaning device for cleaning, sanitizing, and/or disinfecting a stethoscope.

BACKGROUND

In certain healthcare settings, patients on isolation protocol (for MRSA, Cdiff, COVID, etc.) may be treated with dedicated medical equipment rather than shared medical equipment. For example, rather than using a stethoscope that has been used on other patients (e.g., dedicated to a clinical staff member), one stethoscope dedicated to the patient may be placed in the patient's room and used only on that patient.

Since stethoscopes dedicated to an individual patient may be shared by the medical staff, a cleaning device is desirable for cleaning, sanitizing, and/or disinfecting the stethoscope between uses. The embodiments described herein relate to such a device.

BRIEF DESCRIPTION OF THE DRAWINGS

The embodiments discussed herein may be better understood with reference to the following drawings and description. The components in the figures are not necessarily to scale. Moreover, in the figures, like-referenced numerals designate corresponding parts throughout the different views.

DETAILED DESCRIPTION

As discussed in the background above, some healthcare settings require isolation of medical equipment. For example, rather than using a stethoscope dedicated to a single healthcare professional (common in other settings), a patient on isolation protocol may require a stethoscope dedicated to the patient. Optionally (to control costs), these stethoscopes may be relatively low-cost models, such as one of several availed single-patient disposable stethoscope models on the market. Still, supply constraints and/or the overall cost of using many stethoscopes per patient may require the clinical staff to share. The present disclosure describes a stethoscope cleaning device configured for cleaning, disinfecting, and/or sterilizing shared stethoscopes between uses.

Advantageously, the stethoscope cleaning device may prevent pathogens from moving from one clinical staff member to another. Additionally, the stethoscope cleaning device may reduce costs by increasing the lifespan of patient-dedicated stethoscopes. It is also contemplated that such patient-dedicated stethoscope may be higher-quality models (e.g., classic, non-disposable models) without undue cost increases since there may be no need to discard the stethoscope even between numerous uses.

An example of a stethoscope cleaning device 102 is depicted in FIGS. 1-8. The stethoscope cleaning device 102 generally includes a first portion/lower portion 104 and a second portion/upper portion 106. While "upper portion" and "lower portion" are used to describe the depicted examples in the figures, it is noted that in some embodiments, "upper" and "lower" may be switched (or otherwise not apply). The lower portion 104 may be used for receiving, supporting, and cleaning a stethoscope 202, and the upper portion 106 may be used for receiving and supporting a container, such as a canister 302 which stores and dispenses a cleaning fluid (e.g., a liquid, gas, foam, etc.).

The canister 302 (or other container) may include any suitable cleaning fluid known to reduce or eliminate pathogenic agents (such as bacteria) on surfaces. In one non-limiting example, the canister 302 may store a pressurized liquid that includes a substantial amount of ethyl alcohol or another antiseptic along with a foaming agent. This cleaning fluid may be similar (or identical) to certain currently-available hand sanitizers, for example. Advantageously, the stethoscope cleaning device 102 may be compatible with available "off-the-shelf" sanitizer canisters in a reloadable manner.

The stethoscope cleaning device 102 may include aspects that facilitate discharge of the cleaning fluid from the canister 302. For example, certain canisters include a tip 304 that acts as a valve, where the tip 304 prevents the cleaning fluid from escaping when it is in a default state (e.g., where it extends along a central axis 306 of the canister), and where the tip 304 allows outflow from the canister 302 when it is "bent" or otherwise displaced relative to the central axis 306. To accommodate canisters of this type, the upper portion 106 may be pivotable or otherwise displaceable relative to the lower portion 104, where this relative movement causes the tip 304 of the canister 302 to move/bend into an open state (as discussed in more detail below). In other words, movement of the upper portion 106 relative to the lower portion 104 may act as a lever that activates the dispensing tip of the canister.

Figure 1:
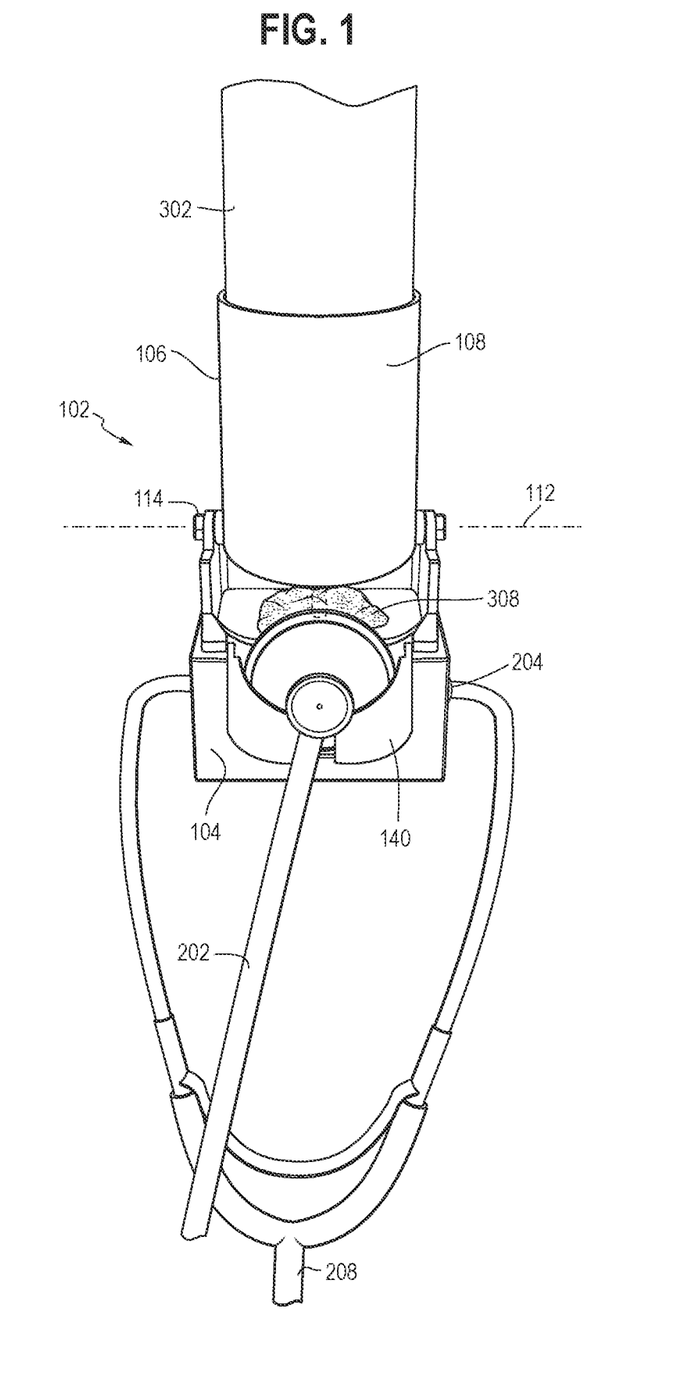
FIG. 1 is an illustration showing an embodiment of a stethoscope cleaning device during a stethoscope cleaning process in accordance with certain aspects of the present disclosure.
Figure 2:
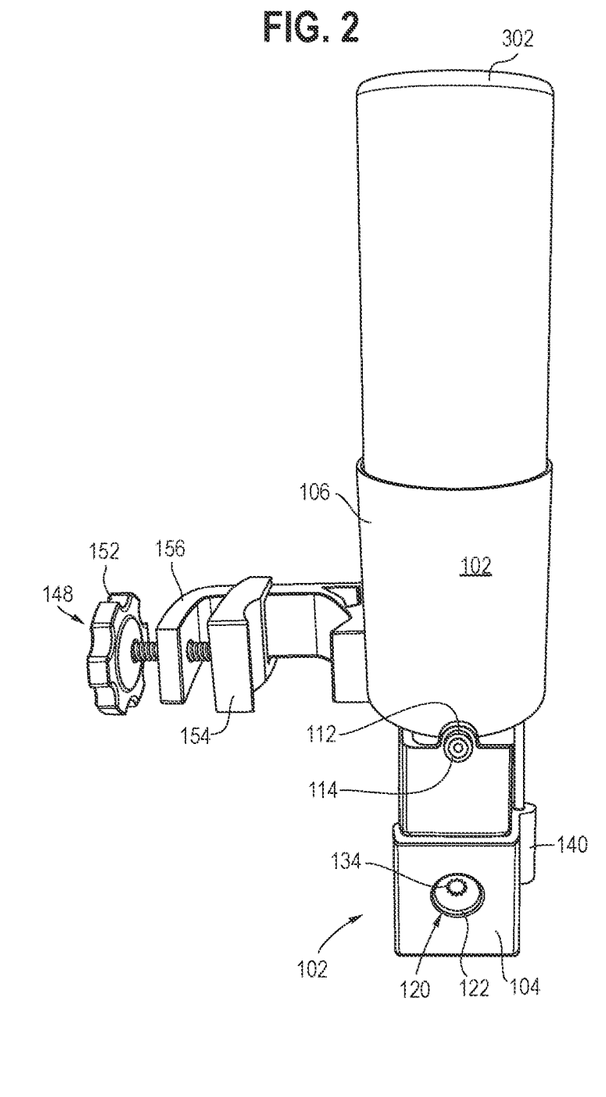
FIG. 2 is an illustration showing a side view of the stethoscope cleaning device from FIG. 1.
Figure 3:
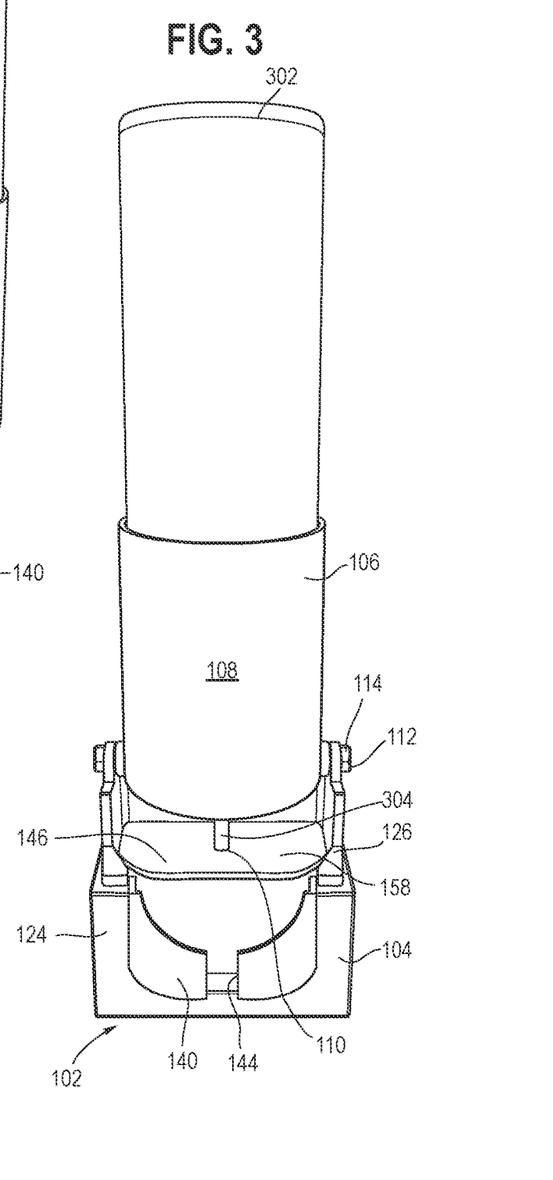
FIG. 3 is an illustration showing a front view of the stethoscope cleaning device from FIGS. 1-2.

The upper portion 106 of the depicted embodiment includes a cylindrical canister holder 108 that is configured (e.g., sized and shaped) to receive and hold the canister 302. As shown in FIGS. 1-3, the canister 302 may be placed in an inverted orientation (with the tip 304 pointing downward). A central opening may be included at the bottom of the canister holder 108 such that the tip 304 may extend out of the canister holder 108 and into a tip opening 110 of the lower portion 104 (e.g., FIGS. 7-8).

Figures 7, 8:
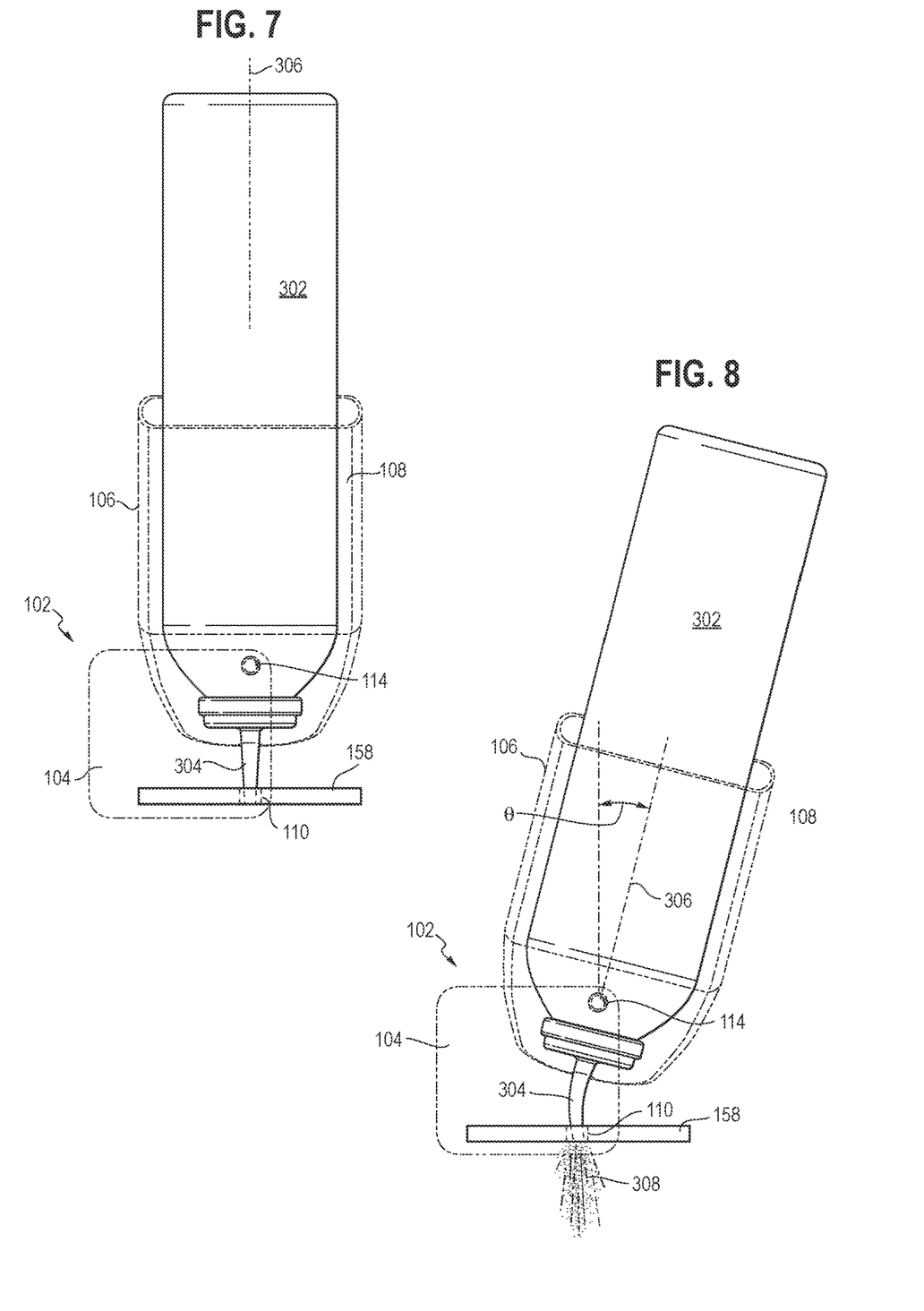
FIG. 7 is an illustration showing a side view of a stethoscope cleaning device in a "closed" or default state, in particular such that a tip of a canister is closed in accordance with certain aspects of the present disclosure.
FIG. 8 is an illustration showing a side view of the stethoscope cleaning device of FIG. 5 in an "open" or cleaning state, in particular such that the tip of the canister is displaced relative to a longitudinal direction of the canister (and therefore allowing flow of a cleaning fluid) in accordance with certain aspects of the present disclosure.

Referring to FIGS. 5-6 and FIGS. 7-8, the upper portion 106 of the stethoscope cleaning device 102 may pivot about a pivot axis 112. This pivoting ability may be provided by a pivot fastener 114 that couples the lower portion 104 to the upper portion 106, such as a screw, rivet, or any other suitable fastener. Thus, when the lower portion 104 pivots relative to the upper portion 106, the tip opening 110 of the lower portion 104 moves relative to the canister holder 108. Since a portion of the canister tip 304 may be within the tip opening 110, this pivoting action may displace the tip 304 from the central axis 306 of the canister 302. To illustrate, as shown in FIG. 2 and FIG. 7, the tip 304 extends along the central axis when the lower portion 104 and the upper portion 106 are in a default, "closed" state. When the upper portion 106 pivots into a cleaning or "open" state shown in FIG. 6 and FIG. 8, the pivoting action causes a terminal end of the tip 304 to displace relative to the remainder of the canister 302, thereby allowing the cleaning fluid 308 to flow out of the canister 302.

Optionally, a spring or other device may be included to cause the upper portion 106 to move into and retain the default, "closed" state relative to the lower portion 104 absent an external actuation force. However, such a spring or other device may not be required when the tip 304 of the canister 302 includes sufficient resilience. For example, the tendency of the stethoscope cleaning device 102 to remain in the default, "closed" state may be provided by the resilience and/or spring characteristics of the canister 302 itself. To overcome this tendency, a user may press on one of the upper portion 106 and/or the lower portion 104 when cleaning is desired. It is contemplated that the hinge action between the upper portion 106 and the lower portion 104 may be optimized with a particular mechanical advantage (e.g., due to a certain radial distance between a location where a user presses on the device and the pivot point).

Figure 4:
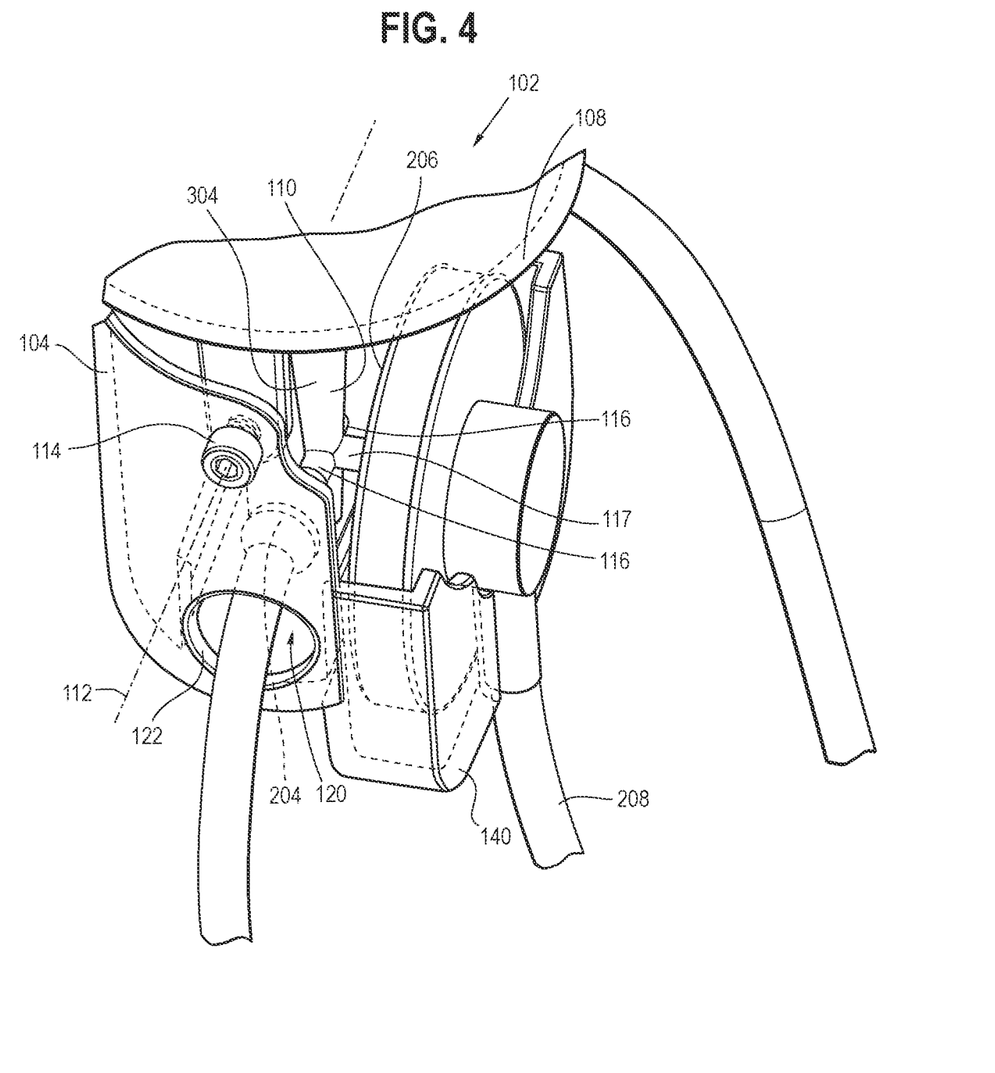
FIG. 4 is an illustration showing a perspective view of a portion of a stethoscope cleaning device having interior channels for directing the flow of a cleaning fluid in accordance with certain aspects of the present disclosure.
Figure 5:
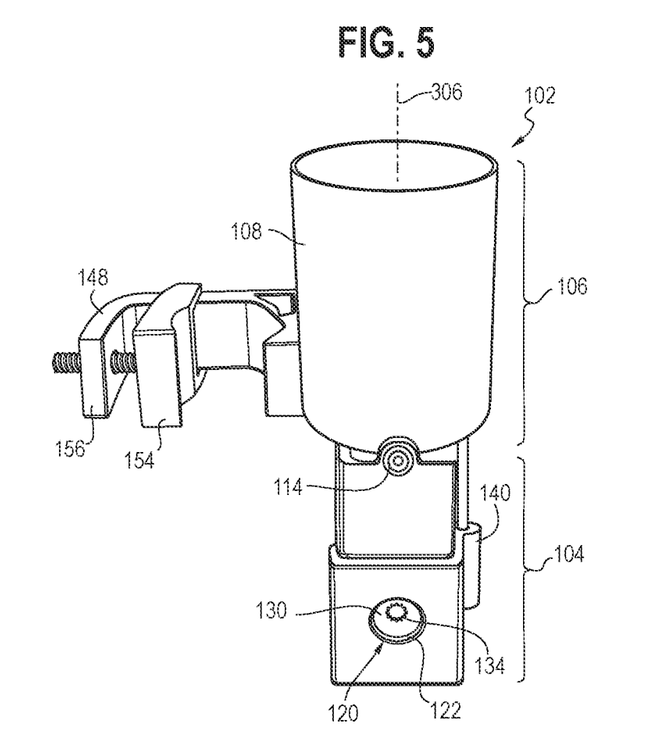
FIG. 5 is an illustration showing a side view of a stethoscope cleaning device in a "closed" or default state in accordance with certain aspects of the present disclosure.
Figure 6:
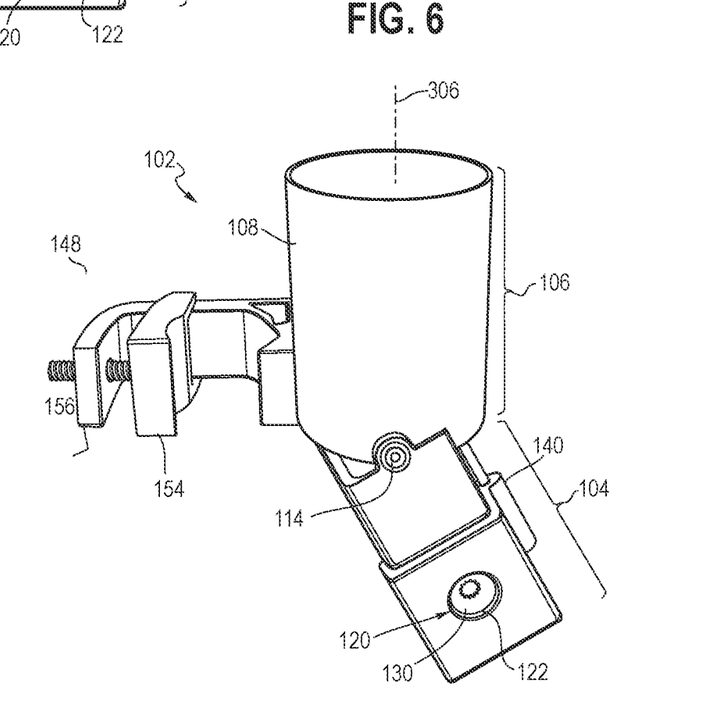
FIG. 6 is an illustration showing a side view of the stethoscope cleaning device of FIG. 5 in an "open" or cleaning state in accordance with certain aspects of the present disclosure.

Referring to FIG. 4, the tip opening 110 of the lower portion 104 may be in fluid communication with one or more cleaning chambers configured to receive earpieces 204 of the stethoscope 202. For example, the tip opening 110 may provide an inlet to one or more channels 116 located inside the lower portion 104 of the stethoscope cleaning device 102, where the channels 116 lead to a set of earpiece cleaning chambers 120. In the depicted example, the channels 116 lead directly to earpiece cleaning chambers 120 such that the cleaning fluid directly flows onto the stethoscope earpieces. In other embodiments (e.g., as discussed with reference to FIG. 9), the flow may be controlled such that the earpieces do not experience direct horizontal flow, which may be advantageous for preventing clogging within earpieces due to inflow of the cleaning fluid. In embodiments that also are configured to clean, disinfect, and/or sanitize the diaphragm 206 of the stethoscope 202, such as the embodiment of FIG. 4, one or more channels 117 may also lead to a chamber or area where the cleaning fluid 308 is dispensed into contact with the diaphragm 206. However, distinct channels are optional, and in some embodiments, the interior of the lower portion 104 may generally fill with the cleaning fluid during stethoscope cleaning, where cleaning chambers or other outlets are in fluid communication with the interior. Other components, orientations, etc. may be included for directing the cleaning fluid through a particularly advantageous flowpath, such as within the embodiment of FIG. 9 discussed below.

As generally shown in FIGS. 1-8, the earpiece cleaning chambers 120 may be accessible via earpiece openings 122 on a first side 124 and a second side 126 of the lower portion 104 of the stethoscope cleaning device 102. The earpiece cleaning chambers 120 may be spaced at a distance such that the stethoscope 202 remains engaged with the stethoscope cleaning device 102 due to resilience within the stethoscope's headset (e.g., "pinching" the earpieces towards the central axis 306 such that they remain in the earpiece openings 122).

Optionally, the earpiece openings 122 may be at least partially covered by a stretchable, compliant membrane 130, which may be formed of a silicone or another suitable compliant/resilient material. The compliant membrane 130 may create a barrier that prevents or limits the cleaning fluid from escaping the device via the earpiece openings 122. The membranes 130 may include membrane openings 134, which may act as the primary point-of-entry of the earpieces 204. Each membrane opening 134 may have a default size that is smaller than an outer diameter of the stethoscope's ear tube, thereby requiring the membrane material to stretch around the ear tube when the earpiece 204 is inserted to create a seal around the ear tube. Additionally or alternatively, the membrane 130 may be advantageous for creating a "squeegee" the cleans/removes excess cleaning fluid from the earpieces 204 as they are removed from the earpiece cleaning chambers 120.

In some embodiments, the stethoscope cleaning device 102 includes a diaphragm holder 140, which is shaped and sized (or otherwise configured) to support the diaphragm 206 of the stethoscope 202. For example, the diaphragm holder 140 may include a receptacle for fitting the bell and diaphragm 206 of the stethoscope 202 along with a central slot 144 for accommodating the stem and tubing 208 of the stethoscope 202.

Since the diaphragm 206 may only contact the isolated patient (and not the clinical staff), it may not need to be cleaned between uses. Nevertheless, the stethoscope cleaning device 102 may be designed such that at least a portion of the cleaning fluid is directed towards the diaphragm 206 when it is properly placed in the diaphragm holder 140. For example, an elongated opening 146 may be located adjacent to the diaphragm holder 140 such that when the interior of the lower portion 104 fills with the cleaning fluid 308, it eventually is forced out of the opening 146. The opening 146 may be located in a place where cleaning fluid may be applied to the patient-facing surface of the diaphragm 206 via direct or indirect flow. In the depicted embodiment, the opening 146 may face vertically such that the diaphragm 206 is indirectly exposed to the flow (which may be advantageous where it is desirable for only a portion of the flow to engage the diaphragm 206). However, other opening orientations, sizes, etc. are also contemplated where different flow characteristics near the diaphragm are desired.

Optionally, the stethoscope cleaning device 102 may include a support interface, such as the depicted pole clamp 148. Advantageously, the pole clamp 148 may allow the stethoscope cleaning device 102 to be coupled to an IV pole or another elongated body. In other embodiments, a wall support interface may be included for attaching the stethoscope cleaning device 102 to a wall, for example. Any other suitable support interface may be additionally or alternatively included.

Figure 9:
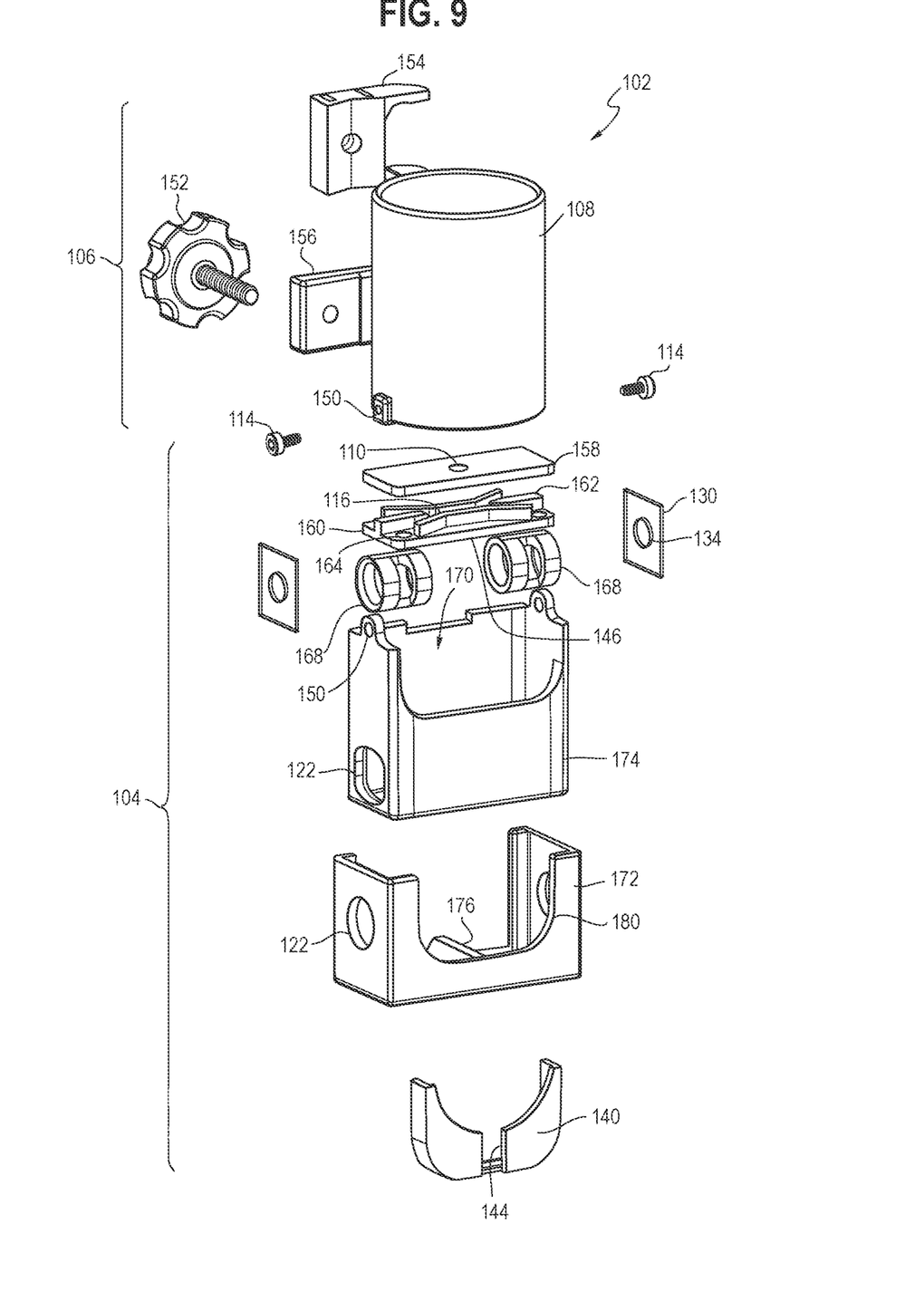
FIG. 9 is an illustration showing an exploded view of an embodiment of a stethoscope cleaning device in accordance with certain aspects of the present disclosure.

FIG. 9 shows an exploded view of one exemplary, non-limiting embodiment of the stethoscope cleaning device 102. Notably, this particular embodiment is shown for purposes of illustration only, and many other embodiments with increased or decreased complexity are also contemplated. The embodiment of FIG. 9 may differ slightly from the embodiment(s) discussed above, particularly within the interior of the lower portion 104. In one specific difference, the channel structure of FIG. 9 is different from that of FIG. 4.

Referring to FIG. 9 and as discussed above, the upper portion 106 may be couplable to the lower portion 104 via a pivot fastener 114, which in this instance is a screw. Corresponding pivot fastener holes 150 may be included in each of the lower portion 104 and the upper portion 106. The upper portion 106 may be fixed to the support interface (in this case the pole clamp 148), although in other embodiments, the support interface may instead be fixed to the lower portion 104. The support interface/pole clamp 148 may generally include a clamp knob 152, a moveable clamp body 154, and a fixed clamp body 156.

The upper portion 106 may include an upper plate 158, which may define the tip opening 110. A channel plate 160 may be located beneath the tip opening 110. As shown, the channel plate 160 may include one or more protrusions 162 that generally defined a set of channels 116 within the interior of the lower portion 104. When the tip 304 of the canister 302 extends through the tip opening 110, a terminus of the tip 304 may be located between the upper plate 158 and the channel plate 160 such that cleaning fluid flowing out of the tip 304 flows through the channels 116.

The channel plate 160 may include openings 164, which act as an outlet from the location between the channel plate 160 and the upper plate 158. In other words, as flow is received through the tip opening 110, the flow of the cleaning fluid may extend over the channel plate 160 (e.g., through the optional channels 116) and then to and through the openings 164 of the channel plate 160.

Figure 10:
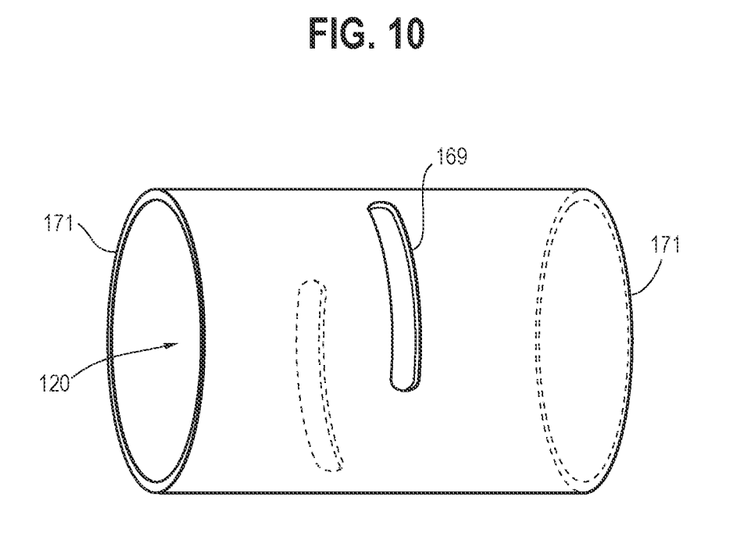
FIG. 10 is an illustration showing a perspective view of an earpiece chamber housing for use with a stethoscope cleaning device in accordance with certain aspects of the present disclosure.

The openings 164 may lead to earpiece chamber housings 168, as shown, which may be cylindrical bodies with openings 171 on each end. The earpiece chamber housings 168 are shown in isolation in FIG. 10. As depicted, the earpiece chamber housings 168 may generally define the earpiece cleaning chambers 120. When assembled, the openings 171 of the earpiece chamber housings 168 may be aligned with the earpiece openings 122 and also the membrane openings 134. Slots 169 within the earpiece chamber housings 168 may be at least partially aligned beneath the openings 164 such that the flow into the earpiece cleaning chambers 120 and onto a stethoscope earpiece is not directed straight into the stethoscope earpiece openings, thereby preventing clogging. As shown, a lengthwise direction of the slots 169 may be perpendicular to a central axis of the cylindrical body of the chamber housing 168, which may create an advantageous direction of flow.

Ultimately, the flow of the cleaning fluid may extend out of the earpiece cleaning chambers and into an interior chamber 170 within the lower portion 104, where the top of the interior chamber 170 is defined by a bottom surface of the channel plate 160. Once a positive pressure is accomplished within the interior chamber 170, the cleaning fluid may be forced out of the interior of the lower portion 104 (e.g., through the diaphragm opening 146 shown in FIG. 3, for example).

The lower portion 104 of the stethoscope cleaning device 102 may include an outer shell 172, which may generally fit around the bottom of an inner housing portion 174. The outer shell 172 may be defined the bottom 176 of the interior chamber 170, for example, and may include one or more curved or angled surfaces for facilitating a particular flow pattern for the cleaning fluid once it enters the interior chamber 170. Advantageously, the design of FIG. 9, including the curved or angled surfaces at the bottom 176 of the interior chamber 170, may prevent stagnant, low-flow areas.

It is contemplated that the outer shell 172 may be removable from the inner housing portion 174 to allow for cleaning of the interior chamber 170 and components within the interior of the lower portion 104. Optionally, the membranes 130 may be located between the inner housing portion 174 and the outer shell 172 when the device is assembled. The outer shell 172 may include a cutout 180 that generally mirrors the outer profile of the diaphragm holder 140. The diaphragm holder 140 may be secured to the inner housing portion 174, the outer shell 172, or both.

Each of the components may be formed with any suitable material, via any suitable manufacturing method. For example, in an exemplary manufacturing method, each the outer shell 172, inner housing portion 174, diaphragm holder 140, canister holder 108, and/or any other suitable portion (and perhaps the majority or entirety of components shown in FIG. 9) are formed with additive manufacturing, such as 3D printing.

While various embodiments have been described, it will be apparent to those of ordinary skill in the art that many more embodiments and implementations are possible. Accordingly, the embodiments described herein are examples, not the only possible embodiments and implementations.

Having described various aspects of the subject matter above, additional disclosure is provided below that may be consistent with the claims originally filed with this disclosure. In describing this additional subject matter, reference may be made to the previously described figures. Any of the following aspects may be combined, where compatible.

One general aspect includes a stethoscope cleaning device, a first portion configured for supporting a stethoscope, where the first portion includes an earpiece chamber for receiving an earpiece of the stethoscope. The stethoscope cleaning device also includes and a second portion configured for receiving a container, where the first portion is movable relative to the second portion, and where movement of the first portion relative to the second portion causes a cleaning fluid to flow from the container to the earpiece chamber.

Implementations may include one or more of the following features. The stethoscope where the movable relationship between the first portion and the second portion includes the first portion being pivotable relative to the second portion, and where pivoting of the first portion relative to the second portion causes a cleaning fluid to flow from the container to the earpiece chamber. The first portion includes tip opening for receiving a tip extending from the container, and where pivoting of the first portion relative to the second portion causes the tip to bend relative to a container body of the container. The tip opening is fixed relative to the earpiece chamber. At least one channel within an interior of the first portion forms at least a portion of a flowpath from the tip opening to the earpiece chamber. The earpiece chamber is at least partially formed with an earpiece chamber housing, and where the earpiece chamber housing includes a cylindrical body having at least one slot in an outer cylindrical surface. The at least one slot is aligned with an opening of a channel plate, and where the opening of the channel plate is in fluid communication with the tip opening. A lengthwise direction of the slot is perpendicular to a central axis of the cylindrical body of the earpiece chamber housing. The stethoscope cleaning device may include a membrane at least partially covering the earpiece chamber, the membrane having a membrane opening configured for stretching upon receipt of the earpiece of the stethoscope. A diaphragm opening is located adjacent to the diaphragm holder, and where the diaphragm opening is in fluid communication with the tip opening. The fixed clamp body is fixed relative to one of the first portion and the second portion.

One general aspect includes a method or forming a stethoscope cleaning device, forming a first portion configured for supporting a stethoscope, where the first portion includes an earpiece chamber for receiving an earpiece of the stethoscope. The method also includes forming a second portion configured for receiving a container. The method also includes and coupling the first portion to the second portion such that the first portion is pivotable relative to the second portion, where pivoting of the first portion relative to the second portion causes a cleaning fluid to flow from the container to the earpiece chamber.

Implementations may include one or more of the following features. The method where the first portion includes tip opening for receiving a tip extending from the container, and where pivoting of the first portion relative to the second portion causes the tip to bend relative to a container body of the container. The tip opening is fixed relative to the earpiece chamber. The earpiece chamber is at least partially formed with an earpiece chamber housing, and where the earpiece chamber housing includes a cylindrical body having at least one slot in an outer cylindrical surface. The method may include a membrane at least partially covering the earpiece chamber, the membrane having a membrane opening configured for stretching upon receipt of the earpiece of the stethoscope. The method may include a diaphragm holder fixed relative to the first portion and configured for supporting a diaphragm of the stethoscope.

One general aspect includes a stethoscope cleaning device, a first portion having an upper plate with an inlet opening a side plate with a first earpiece chamber and a second earpiece chamber. The stethoscope cleaning device also includes and a second portion having a container holder, where the first portion is pivotable relative to the second portion about a pivot axis defined by a pivot fastener.

Implementations may include one or more of the following features. The stethoscope cleaning device where the inlet opening of the first portion is configured for receiving a tip of a canister placed within the container holder of the second portion such that pivotable movement of the first portion relative to the second portion is configured to cause bending of the tip. The inlet opening is in fluid communication with the first earpiece chamber and the second earpiece chamber.

We claim:

1. A stethoscope cleaning device, comprising:
   a first portion configured for supporting a stethoscope, wherein the first portion includes an earpiece chamber for receiving an earpiece of the stethoscope; and
   a second portion configured for receiving a container, wherein the first portion is movable relative to the second portion, and
   wherein movement of the first portion relative to the second portion causes a cleaning fluid to flow from the container to the earpiece chamber.

2. The stethoscope cleaning device of claim 1, wherein the movable relationship between the first portion and the second portion includes the first portion being pivotable relative to the second portion, and wherein pivoting of the first portion relative to the second portion causes a cleaning fluid to flow from the container to the earpiece chamber.

3. The stethoscope cleaning device of claim 1, wherein the first portion includes tip opening for receiving a tip extending from the container, and wherein pivoting of the first portion relative to the second portion causes the tip to bend relative to a container body of the container.

4. The stethoscope cleaning device of claim 3, wherein the tip opening is fixed relative to the earpiece chamber.

5. The stethoscope cleaning device of claim 3, wherein at least one channel within an interior of the first portion forms at least a portion of a flowpath from the tip opening to the earpiece chamber.

6. The stethoscope cleaning device of claim 1, wherein the earpiece chamber is at least partially formed with an earpiece chamber housing, and wherein the earpiece chamber housing includes a cylindrical body having at least one slot in an outer cylindrical surface.

7. The stethoscope cleaning device of claim 6, wherein the at least one slot is aligned with an opening of a channel plate, and wherein the opening of the channel plate is in fluid communication with the tip opening.

8. The stethoscope cleaning device of claim 6, wherein a lengthwise direction of the at least one slot is perpendicular to a central axis of the cylindrical body of the earpiece chamber housing.

9. The stethoscope cleaning device of claim 1, further comprising a membrane at least partially covering the earpiece chamber, the membrane having a membrane opening configured for stretching upon receipt of the earpiece of the stethoscope.

10. The stethoscope cleaning device of claim 1, further comprising a diaphragm holder fixed relative to the first portion and configured for supporting a diaphragm of the stethoscope, wherein a diaphragm opening is located adjacent to the diaphragm holder, and wherein the diaphragm opening is in fluid communication with the tip opening.

11. The stethoscope cleaning device of claim 1, further comprising a pole clamp having a moveable clamp body and a fixed clamp body, and wherein the fixed clamp body is fixed relative to one of the first portion and the second portion.

12. A method or forming a stethoscope cleaning device, the method comprising:
   forming a first portion configured for supporting a stethoscope, wherein the first portion includes an earpiece chamber for receiving an earpiece of the stethoscope;
   forming a second portion configured for receiving a container; and
   coupling the first portion to the second portion such that the first portion is pivotable relative to the second portion,
   wherein pivoting of the first portion relative to the second portion causes a cleaning fluid to flow from the container to the earpiece chamber.

13. The method of claim 12, wherein the first portion includes a tip opening for receiving a tip extending from the container, and wherein pivoting of the first portion relative to the second portion causes the tip to bend relative to a container body of the container.

14. The method of claim 13, wherein the tip opening is fixed relative to the earpiece chamber.

15. The method of claim 12, wherein the earpiece chamber is at least partially formed with an earpiece chamber housing, and wherein the earpiece chamber housing includes a cylindrical body having at least one slot in an outer cylindrical surface.

16. The method of claim 12, further comprising a membrane at least partially covering the earpiece chamber, the membrane having a membrane opening configured for stretching upon receipt of the earpiece of the stethoscope.

17. The method of claim 12, further comprising a diaphragm holder fixed relative to the first portion and configured for supporting a diaphragm of the stethoscope.

\* \* \* \* \*